(12) United States Patent
De Voir et al.

(10) Patent No.: US 7,985,185 B2
(45) Date of Patent: Jul. 26, 2011

(54) HEART MONITORING APPARATUS

(75) Inventors: Christopher S. De Voir, Tigard, OR (US); Dirk Muessig, West Linn, OR (US); Sharon Lefkov, Portland, OR (US); Michael V. Orlov, Brookline, MA (US)

(73) Assignee: Biotronik CRM Patent AG, Baar (CH)

( * ) Notice: Subject to any disclaimer, the term of this patent is extended or adjusted under 35 U.S.C. 154(b) by 483 days.

(21) Appl. No.: 12/132,477

(22) Filed: Jun. 3, 2008

(65) Prior Publication Data

US 2009/0299203 A1 Dec. 3, 2009

(51) Int. Cl.
*A61B 5/04* (2006.01)
*A61B 5/02* (2006.01)
(52) U.S. Cl. ......... 600/508; 600/374; 600/483; 600/509
(58) Field of Classification Search .................. 600/374, 600/483, 506–509
See application file for complete search history.

(56) References Cited

U.S. PATENT DOCUMENTS

| 5,792,194 | A * | 8/1998 | Morra .......................... 607/17 |
| 6,285,898 | B1 * | 9/2001 | Ben-Haim ................... 600/374 |
| 2006/0253043 | A1 * | 11/2006 | Zhang et al. ................. 600/512 |
| 2007/0255327 | A1 * | 11/2007 | Cho et al. ..................... 607/18 |

* cited by examiner

*Primary Examiner* — Niketa I Patel
*Assistant Examiner* — Nicole F Lavert
(74) *Attorney, Agent, or Firm* — ARC IP Law, PC; Joseph J. Mayo

(57) ABSTRACT

Heart monitoring apparatus with sensing stage connectable to intracardiac electrode picking up electric potentials and adapted to process electric signals representing a time course of said potentials, a mechanical action detection stage adapted to generate a geometry signal having a time course reflecting heart chamber's geometry change, an evaluation unit connected to sensing stage and impedance measuring stage and adapted to determine a first and second fiducial point in the time course of said potentials and geometry signal, respectively, both fiducial points belonging to same heart cycle, and to determine a measured time delay between said fiducial points. Evaluation unit adapted to repeat said determined time delay to determine plurality of measured time delays and variance thereof or divergence of the statistical properties of cycle times based on said time course of said electric potentials versus cycle times based on said time course reflecting a change of a heart chamber's geometry.

13 Claims, 11 Drawing Sheets

HEART MONITORING APPARATUS

BACKGROUND OF THE INVENTION

1. Field of the Invention

The invention relates to a heart monitoring apparatus. According to a preferred aspect of the invention, the heart monitoring apparatus is incorporated in an implantable medical device such as an implantable pacemaker, implantable cardioverter/defibrillator or a combination thereof.

2. Description of the Related Art

Such implantable medical devices are used to help patients suffering from some type of heart failure (HF) such as congestive heart failure (CHF) and the like. The implantable medical device shall ideally choose a therapy mode best suiting a patient's health state by automatic determination of the health state.

A typical pacemaker has at least one stimulation pulse generator to selectively generate stimulation pulses for delivery to at least two different chambers of a heart, said chambers include right and left atria and right and left ventricles. Said one stimulation pulse generator may be switchable in order to generate stimulation pulses for different chambers of the heart. In general, however, separate stimulation pulse generators will be provided for each heart chamber to be stimulated. The timing and triggering of stimulation pulses is typically controlled by a control unit. Time intervals to be timed by the control unit may, among other things, include an atrioventricular time delay (AVD) between an atrial event and a ventricular event and/or an interventricular delay (VVD) between a right ventricular event and a left ventricular event.

State of the art pacemakers include means to optimize the atrioventricular and/or the interventricular delay based on a hemodynamic sensor information.

For AVD optimization, the pacemaker provides for at least one atrial and one ventricular channel for pacing and/or sensing. For VVD optimization, the pacemaker provides for pacing channels for both ventricles.

A pacemaker shall help a heart suffering from some disorder to perform similarly to a healthy heart.

In a healthy heart, initiation of the cardiac cycle normally begins with depolarization of the sinoatrial (SA) node. This specialized structure is located in the upper portion of the right atrium wall and acts as the natural "pacemaker" of the heart. In a normal cardiac cycle and in response to the initiating SA depolarization, the right atrium and left atrium contract and force the blood that has accumulated therein into the ventricles. The natural stimulus causing the right atrium and left atrium to contract is conducted to the right ventricle and left ventricle via the atrioventricular node (AV node) with a short, natural delay, the atrioventricular delay (AV-delay, AVD). Thus, a short time after the right atrial and left atrial contraction (a time sufficient to allow the bulk of the blood in the atria to flow through the one-way valves into the ventricles), the ventricles contract, forcing the blood out of the ventricles to the lungs and body tissue. A typical time interval between contraction of the atria and contraction of the ventricles might be 60 ms; a typical time interval between contraction of the ventricles and the next contraction of the atria might be 800 ms. Thus, it is a right atrial and left atrial contraction (A), followed a relatively short time thereafter by a right ventricle and left ventricle contraction (V), followed by a relatively long time thereafter by the next right atrial and left atrial contraction, that produces the desired AV synchrony. Where AV synchrony exists, the heart functions very efficiently as a pump in delivering life-sustaining blood to body tissue; where AV synchrony is absent, the heart functions as an inefficient pump (largely because the right ventricle is contracting when it is not maximally filled with blood).

In addition to proper filling time with respect to the atria, the positive or negative time delay between the right and left ventricles determines the degree to which they provide a mechanical advantage to each other during contraction due to their common point of attachment (the apex) and shared wall (the septum).

A pacemaker generally shall induce a contraction of a heart chamber by delivery of a stimulation pulse (pacing pulse) to said chamber when no natural (intrinsic) stimulation of said chamber occurs in due time. A contraction of a heart chamber often is called "event." Since a stimulation may be an intrinsic stimulation, which can be sensed by a sensing stage of a pacemaker, such event is called a sensed event. A stimulation due to delivery of a stimulation pulse is called a paced event. A sensed event in the atrium is called As, a paced atrial event is called Ap. Similarly, a sensed event in the ventricle is called Vs and a paced ventricular event is called Vp.

To mimic the natural behavior of a heart, a dual-chamber pacemaker provides for an AV-delay timer to provide for an adequate time delay (AV-delay, AVD) between a natural (intrinsic) or a stimulated (paced) right atrial stimulation and a right ventricular stimulation. In a similar way, a biventricular pacemaker provides for an adequate time delay (VV-delay, VVD) between a right ventricular stimulation and a left ventricular stimulation.

The time delay for a left ventricular (stimulated, paced) contraction may be timed from a scheduled right ventricular stimulation, which has not yet occurred or from a natural (intrinsic) or a stimulated (paced) right atrial contraction. In the latter case, a left ventricular stimulation pulse is scheduled by a time interval AVD+VVD.

To deal with possibly occurring natural (intrinsic) atrial or ventricular stimulations, a demand pacemaker schedules a stimulation pulse for delivery at the end of the AV-delay or the VV-delay, respectively. The delivery of said stimulation pulse is inhibited, if a natural stimulation of the heart chamber to be stimulated is sensed within the respective time delay.

Ventricular pacing in one or both ventricles is required for patients with AV-block and for CHF patients that are indicated for cardiac resynchronization therapy (CRT). For patients with intact sinus rhythm or with effective atrial pacing, it is beneficial to stimulate the ventricle(s) synchronous with the atrial activation, i.e., after a certain delay period after the atrial event. Standard AV-synchronous dual- or three-chamber implantable devices have a programmable AVD that can be adjusted by the physician. Several studies have shown the importance of individual AVD optimization to improve the cardiac output. Especially for CHF patients, optimization of the AVD is essential. As the pumping efficacy is impaired, the optimal timing of the ventricular stimulus in relation to the atrial event contributes significantly to the cardiac performance. If the AVD is too short, the ventricle contracts before it is completely filled by the atrial blood inflow. The active filling time is reduced. Hence the stroke volume and the cardiac output are reduced. If the AVD is too long, the ventricle contracts a while after the closure of the atrioventricular valve. Hence the passive filling time of the ventricle, i.e., the diastolic filling period during the myocardial relaxation before the atrial kick, is decreased. Also backflow of blood from the ventricle into the atrium, e.g., mitral regurgitation, is likely. Thus also in this case cardiac output (CO) is reduced. Similar to the heart rate, the optimal AVD also depends on the activation state of the circulation. If the sympathetic tone is high, e.g., during exercise, the optimal AVD is shortened compared to the resting value.

Patients with CHF and Left Bundle-Branch Block (LBBB), i.e., with interventricular dyssynchrony expressed by a widened QRS complex in the electrogram, may benefit from biventricular pacing. Pacing both ventricles simultaneously or with a certain VVD restores the synchrony of the ventricles and thus improves the hemodynamic performance. Also mitral regurgitation may be reduced by biventricular pacing. Recent CRT pacing devices, implantable pulse generators (IPGs) or ICDs, offer a programmable VVD parameter. The delay time between the right ventricular (RV) and left ventricular (LV) stimulation can be programmed, usually approx. in the range −100 ms . . . +100 ms. The sign determines whether the RV or the LV is paced first. 0 ms means simultaneous pacing of both ventricles. Also RV or LV-only pacing can be programmed. It has been found that the setting resulting in optimal hemodynamics varies individually from patient to patient. The optimal value also depends on the individual position of the left ventricular pacing lead, which usually is located in a lateral coronary vein, or less often on the left epicardium.

Some prior art pacemakers include at least one impedance measuring stage being connected to electrodes or a connector for such electrodes to measure an intracardiac impedance when in use.

For CRT optimization presently the following techniques are applied:
1. Echocardiographic techniques to optimize AV and/or VV intervals that are expensive, time consuming and can only be done periodically, not continuously. These techniques are frequently unreliable and poorly reproducible.
2. Automatic AV/VV optimization at Follow up based on intracardiac electric assumptions. This is not a continuous method, and while less costly and less time consuming than echo, it is still periodic. Clinical utility and reproducibility of these methods remain to be proven.

To monitor heart failure status presently the following techniques are applied:
1. Monitoring of pulmonary edema. Pulmonary edema is a very late sign of worsening heart failure. So far, the sensitivity and specificity of the known monitor have been low (approx 60%).
2. Direct monitoring of left atrial pressure. This requires a separate sensor (from IMD and leads) and directly accesses the left atrium which could put a patient at increased risk of bleeding, infection, or embolism.

Problems Not Solved so Far are:

Early detection of HF before the development of pulmonary edema. Reveal this early stage by monitoring transthoracic and intracardiac impedance signals.

Atypical forms of HF may not show usual signs, for example, HF may show no indication of conduction system defect or change in QRS width. The proposed solution is to reveal this atypical HF by detecting the weakening of the relationship between the electrical and mechanical events of LV function caused by a developing HF.

30% of patients with CRT are non-responders. The proposed solution is to optimize CRT by tracking the response to therapy by monitoring electromechanical coupling events and adjusting IMD parameters automatically.

Objective measures of optimal medical therapy for the treatment of HF do not exist. The proposed solution identifies a device-based measure that can determine a physiological (i.e. electromechanical coupling) response to medical intervention.

BRIEF SUMMARY OF THE INVENTION

It is an objective of the invention to provide a heart monitoring apparatus providing improved monitoring capabilities and thus allowing for improved adaptation of therapy to a patient's health state. In particular, the invention shall identify a device based measure that can determine a physiological (i.e. electromechanical coupling) response to medical intervention.

According to the invention, this object is achieved by a heart monitoring apparatus comprising:
- at least one sensing stage connected or connectable to at least one intracardiac electrode for picking up electric potentials of a myocardium of a heart's ventricle or atrium, said sensing stage being adapted to process electric signals representing a time course of said electric potentials,
- a least one mechanical action detection stage adapted to generate a geometric signal reflecting mechanical action of a heart chamber, said geometric signal having a time course reflecting a change of a heart chamber's geometry,
- an evaluation unit being connected to said sensing stage and to said impedance measuring stage, being adapted to determine a first fiducial point in the time course of said electric potentials, and a second fiducial point in the time course of said intracardiac impedance or conductance, said first fiducial point and said second fiducial point belonging to the same heart cycle, and to determine a time delay between said fiducial points,
- said evaluation unit being further adapted to repeat said determination of said time delay between two fiducial points to thus determine a plurality of time delays,
- and to determine a variance of said plurality of time delays or a divergence of the statistical properties of cycle times that are based on said time course of said electric potentials versus cycle times that are based on said time course reflecting a change of a heart chamber's geometry.

The apparatus is thus able to provide an indication of changes in the status of heart failure (HF) patients, by detecting changes in the electromechanical coupling of electrical and mechanical events within the heart.

Preferably, the mechanical action detection stage is an impedance measuring stage connected or connectable to at least two intracardiac electrodes and is adapted to determine a time course of an intracardiac impedance or conductance signal, reflecting an intracardiac impedance or conductance being effective between said intracardiac electrodes, said intracardiac impedance or conductance signal being said geometric signal. Thus, the detection in the electromechanical coupling of electrical and mechanical events is accomplished by monitoring the dispersion characteristics of the intracardiac electrogram (IEGM), versus the intracardiac impedance measurements.

It is further preferred, if the evaluation unit is adapted to determine a maximum in a time course of the intracardiac impedance or a minimum in the time course of the intracardiac conductance as a second fiducial point related to said impedance or conductance, respectively. It is to be noted, that since conductance is inverse to impedance, conductance and impedance may be evaluated equally for the purpose of this invention, although most parts of the following description will refer to impedance only. Basically, any suitable measurement for determining the time point of minimum heart chamber volume and the end of cardiac systole may be applied for carrying out the invention. Since changes in the intracardiac impedance and the intracardiac conductance are mainly caused by a change of volume of a respective heart chamber, intracardiac impedance and intracardiac conductance are suitable indicators of mechanical heart action. This is because the conductance of blood in the heart chamber is higher than the conductance of the heart tissue (myocardium) enclosing a heart chamber.

Preferably, the sensing stage is adapted to detect cardiac events representing a depolarization of the myocardium by processing said electric signals representing a time course of said electric potentials, wherein said cardiac event marks a first fiducial point in said time course of said electric potentials.

According to a preferred embodiment of the invention, the evaluation unit is adapted to determine the divergence of the statistical properties of IEGM and impedance based cycle times and to generate an output signal that indicates a state of HF, when the divergence exceeds a predetermined threshold value.

BRIEF DESCRIPTION OF THE DRAWINGS

The above and other aspects, features and advantages of the present invention will be more apparent from the following more particular description thereof, presented in conjunction with the following drawings wherein.

DETAILED DESCRIPTION OF THE INVENTION

The following description is of the best mode presently contemplated for carrying out the invention. This description is not to be taken in a limiting sense, but is made merely for the purpose of describing the general principles of the invention. The scope of the invention should be determined with reference to the claims.

Figure 1:
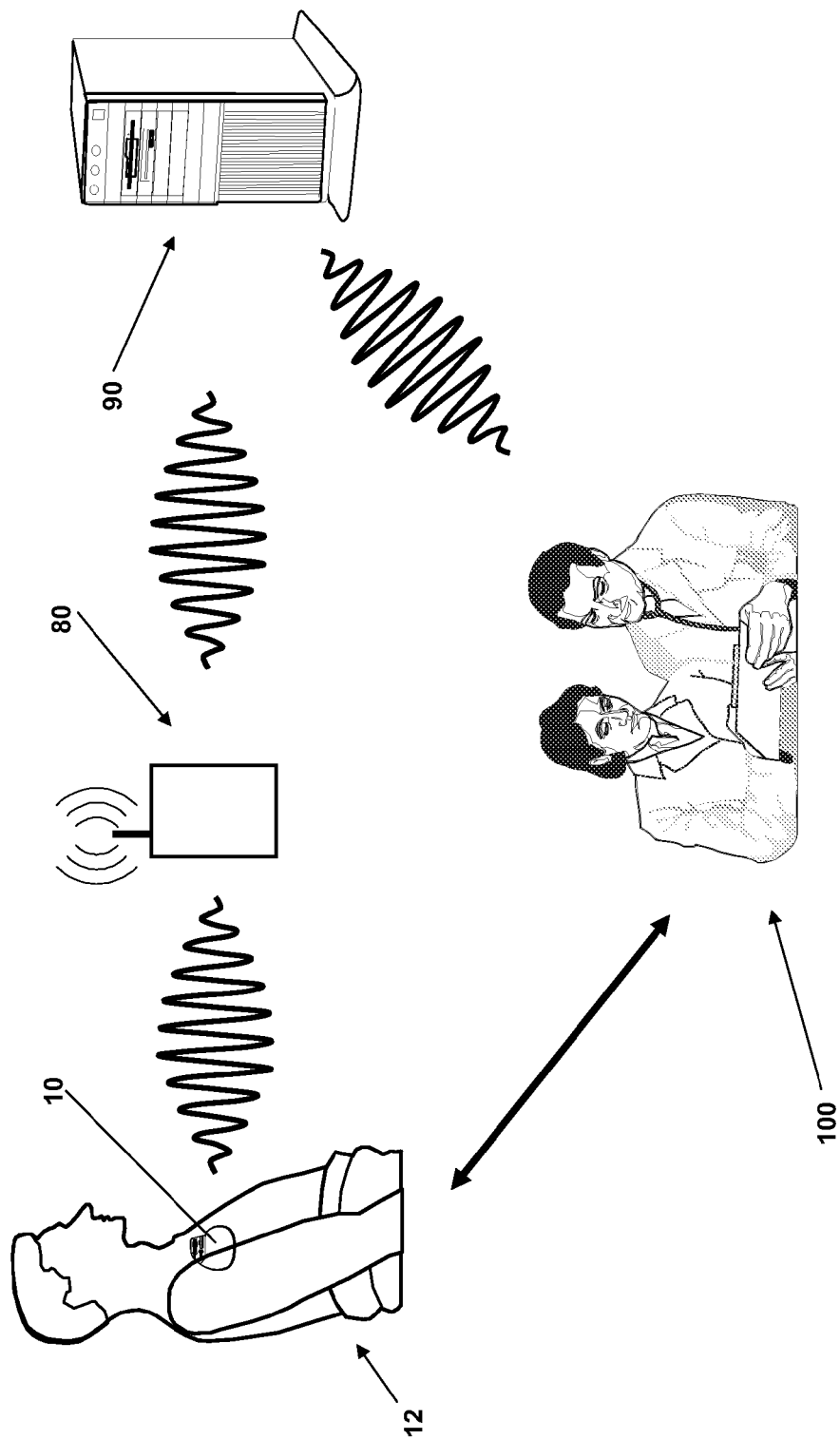
FIG. 1 is a schematic overview of a heart monitoring system comprising an implantable medical device, an external transceiver device and a service center.

FIG. 1 shows a heart monitoring apparatus incorporated in an implantable medical device 10. The implantable medical device is part of an implantable device system further comprising an external transceiver device 80 and a central service center 90. The implantable medical device 10 is for example an implantable pacemaker or an implantable cardio-verter/defibrillator or a combination of both. The implantable medical device 10 comprises an implant transceiver for wireless communication with the external transceiver device 80. The external transceiver device 80 comprises an external transceiver unit (not shown) for wireless communication with the implant transceiver unit and a data communication interface (also not shown) adapted to allow a data communication with the service center 90. The data communication interface preferably is adapted to use a public data communication line such as a telephone landline connection or wireless connection via GPRS or SMS.

The central service center 90 comprises or is connected to a user interface allowing a physician or a team of physicians to interact with the central service center. The user interface may comprise a display for displaying data to the physician (100) and some input device allowing the physician (100) to enter instructions or data into the central service center 90. The central service center 90 further comprises a central data base that is connected to said data communication interface (see FIG. 3) and a data evaluation module that is connected to the data base that is adapted to evaluate data stored and said data base.

Figure 2:
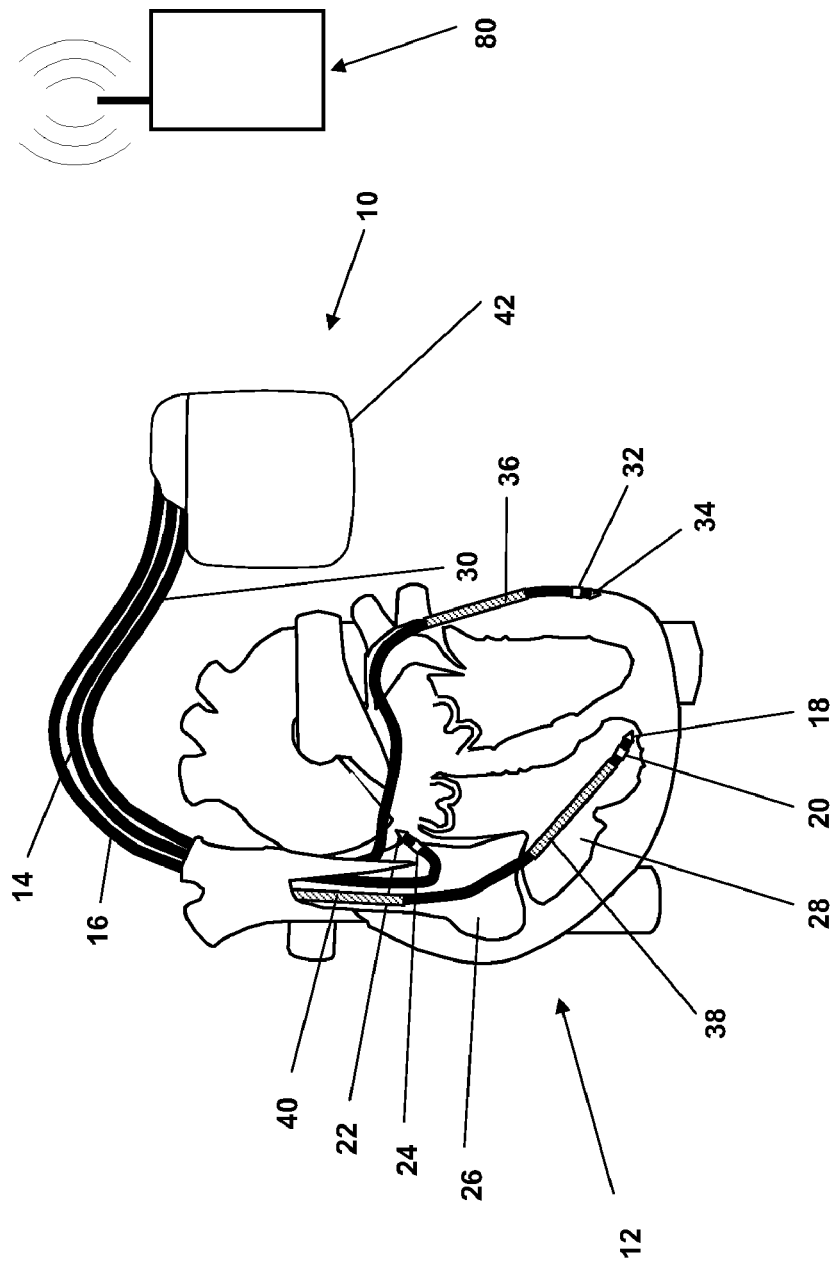
FIG. 2 shows a three chamber bi-ventricular implantable cardioverter/defibrillator (ICD).

In FIG. 2 the implantable medical device is a three chamber biventricular pacemaker and cardioverter/defibrillator 10 that is connected to pacing/sensing leads placed in a heart 12 is illustrated.

As shown in FIG. 2, the preferred embodiment is to couple the disclosed technology with an implantable bi-ventricular defibrillator.

The implantable medical device 10 is electrically coupled to heart 12 by way of leads 14, 16 and 30.

Lead 14 is a right atrial electrode lead that has a pair of right atrial electrodes 22 and 24 that are in contact with the right atrium 26 of the heart 12.

Lead 16 is a right ventricular electrode lead that has a pair of ventricular stimulation and sensing electrodes 18 and 20 that are in contact with the right ventricle 28 of heart 12. Further, a ventricular defibrillation shock coil 38 and an atrial defibrillation shock coil 40 are arranged on lead 16.

Electrodes 22 and 18 are tip electrodes at the very distal end of leads 14 and 16, respectively. Electrode 22 is a right atrial tip electrode RA Tip and electrode 18 is a right ventricular tip electrode. Electrodes 24 and 20 are ring electrodes in close proximity but electrically isolated from the respective tip electrodes 22 and 18. Electrode 24 forms a right atrial ring electrode RA Ring and electrode 20 forms a right ventricular ring electrode RV Ring. Atrial cardioversion shock coil 40 is a coil electrode providing a relatively large geometric area when compared to the stimulation electrodes 18, 20, 22 and 24.

Lead 30 is a left ventricular electrode lead passing through the coronary sinus of heart 12 and having a left ventricular ring electrode LV RING 32, and a left ventricular tip electrode LV TIP 34. Further, a left ventricular defibrillation shock coil 36 may be arranged on lead 30.

Implantable medical device 10 has a case 42 made from electrically conductive material such as titanium that can serve as a large surface electrode IMD CASE.

The plurality of electrodes 18, 20, 22, 24, 32, 34, 36, 38 and 40 connected to implantable medical device 10 together with case 42 allow for a number of different electrode configurations for measuring intrathoracic and intracardiac impedance.

The forcing function for intrathoracic impedance measurement preferably is sourced via the right ventricular or a left ventricular ring electrode and the current sink would be the implantable medical device's case. Measurement of the response function preferably is carried out between a right ventricular tip electrode and the implantable medical device's case or a left ventricular tip electrode and the implantable medical device's case.

For intracardiac impedance measurements, the following configuration is preferred, but not limited to, injecting a forcing function from a right ventricular ring electrode to a right ventricular tip electrode and measuring a response function between a left ventricular ring electrode and a left ventricular tip electrode. This would be configuration Quadrapolar #2 from Table 1 below.

The purpose for the selection of any measurement configuration is to maximize the proximity to and alignment with the changing geometry. Further possible electrode configurations for application of the forcing function and measurement of the response function become apparent from the following table:

TABLE 1

Selected impedance configurations.

| Diagnostic Value | Polarity | Forcing contacts | Response contacts |
| --- | --- | --- | --- |
| Primary | Tripolar | RV Ring to Case | RV Tip to Case |
| Primary | Tripolar | LV Ring to Case | LV Tip to Case |
| Primary | Bipolar | RV Coil to Case | RV Coil to Case |
| Primary | Bipolar | LV Coil to Case | LV Coil to Case |
| Secondary | Quadrapolar #1 | LV Ring to RV Ring | LV Tip to RV Tip |
| Secondary | Quadrapolar #2 | RV Ring to RV Tip | LV Ring to LV Tip |
| Secondary | Tripolar | RV Ring to LV Ring | RV Tip to LV Ring |
| Secondary | Tripolar | RV Ring to LV Tip | RV Tip to LV Tip |
| Secondary | Tripolar | LV Ring to RV Ring | LV Tip to RV Ring |
| Secondary | Tripolar | LV Ring to RV Tip | LV Tip to RV Tip |
| Secondary | Bipolar | RV Ring to LV Ring | RV Ring to LV Ring |
| Secondary | Bipolar | RV Tip to LV Tip | RV Tip to LV Tip |
| Secondary | Bipolar | RV Ring to LV Tip | RV Ring to LV Tip |
| Secondary | Bipolar | RV Tip to LV Ring | RV Tip to LV Ring |

Figure 3A:
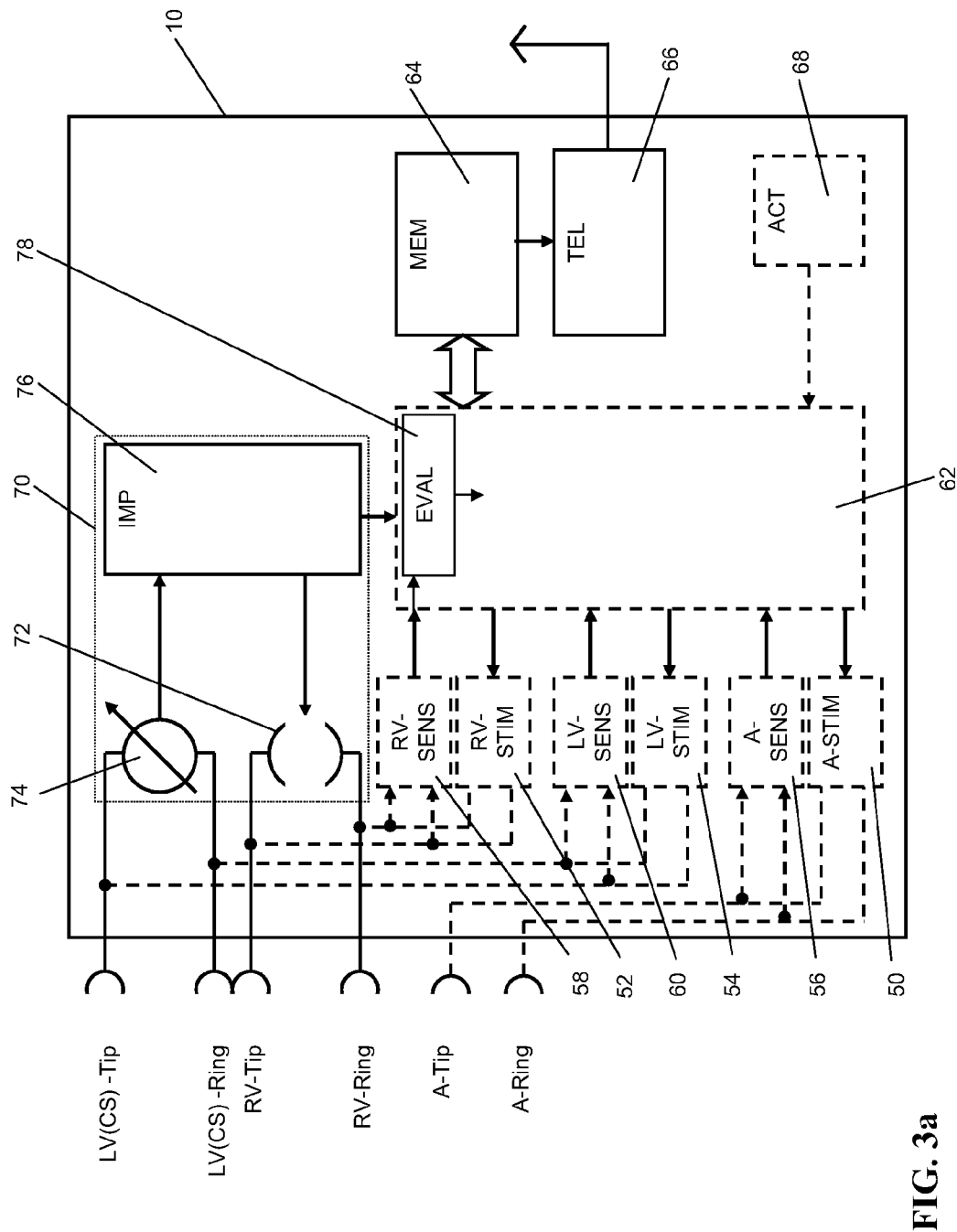
FIGS. 3a to 3c are schematic diagrams of three alternative embodiments of the device modules of the ICD of FIG. 3.

Referring to FIG. 3a illustrating a simplified block diagram of an implantable medical device 10. During operation of the pacemaker leads 14, 16 and 30 are connected to respective output/input terminals of pacemaker 10 as indicated in FIG. 2 and carry stimulating pulses to the tip electrodes 18, 22 and 34 from a right atrial stimulation pulse generator A-STIM 50, a right ventricular pulse generator RV-STIM 52 and a left ventricular pulse generator LV-STIM 54, respectively. Further, electrical signals from the right atrium are carried from the electrode pair 22 and 24, through the lead 14, to the input terminal of a right atrial channel sensing stage A-SENS 56; and electrical signals from the right ventricle are carried from the electrode pair 18 and 20, through the lead 16, to the input terminal of a right ventricular sensing stage RV-SENS 58. Likewise electrical signals from the left ventricle are carried from the electrode pair 32 and 34, through the lead 30, to the input terminal of a left ventricular sensing stage LV-SENS 60. Controlling the implantable medical device 10 is a control unit CTRL 62 that is connected to sensing stages A-SENS 56, RV-SENS 58 and LV-SENS 60 and to stimulation pulse generators A-STIM 50, RV-STIM 52 and LV-STIM 54. Control unit CTRL 62 receives the output signals from the atrial sensing stage A-SENS 56, from the right ventricular sensing stage RV-SENS 58 and from the left ventricular sensing stage LV-SENS 60. The output signals of sensing stages A-SENS 56, RV-SENS 58 and LV-SENS 60 are generated each time that a P-wave representing an intrinsic atrial event or an R-wave representing an intrinsic ventricular event, respectively, is sensed within the heart 12. An As-signal is generated, when the atrial sensing stage A-SENS 56 detects a P-wave and a RVs-signal is generated, when the right ventricular sensing stage RV-SENS 58 detects an R-wave.

These sense events are used by control unit CTRL 62 as fiducial points of the respective intracardiac electrograms picked up by the sensing stages A-SENS 56, RV-SENS 58 and LV-SENS 60, respectively.

Control unit CTRL 62 also generates trigger signals that are sent to the atrial stimulation pulse generator A-STIM 50, the right ventricular stimulation pulse generator RV-STIM 52 and the left ventricular stimulation pulse generator LV-STIM 54, respectively. These trigger signals are generated each time that a stimulation pulse is to be generated by the respective pulse generator A-STIM 50, RV-STIM 52 or LV-STIM 54. The atrial trigger signal is referred to simply as the "A-pulse", and the ventricular trigger signal is referred to as the "RV-pulse" or the "LV-pulse", respectively. During the time that either an atrial stimulation pulse or ventricular stimulation pulse is being delivered to the heart, the corresponding sensing stage, A-SENS 56, RV-SENS 58 and/or LV-SENS 60, is typically disabled by way of a blanking signal presented to these amplifiers from the control unit CTRL 62, respectively. This blanking action prevents the sensing stages A-SENS 56, RV-SENS 58 and LV-SENS 60 from becoming saturated from the relatively large stimulation pulses that are present at their input terminals during this time. This blanking action also helps prevent residual electrical signals present in the muscle tissue as a result of a stimulation pulse delivered from pacemaker 10 from being interpreted as P-waves or R-waves.

Furthermore, atrial sense events As recorded shortly after delivery of a ventricular stimulation pulse during a preset time interval called post ventricular atrial refractory period (PVARP) are generally recorded as atrial refractory sense event Ars but ignored.

Control unit CTRL 62 comprises circuitry for timing ventricular and/or atrial stimulation pulses according to an adequate stimulation rate that can be adapted to a patient's hemodynamic need as pointed out below.

Still referring to FIG. 3, the implantable medical device 10 includes a memory circuit MEM 64 that is coupled to the control unit CTRL 62 over a suitable data/address bus ADR. This memory circuit MEM 64 allows certain control parameters, used by the control unit CTRL 62 in controlling the operation of the implantable medical device 10, to be programmably stored and modified, as required, in order to customize the implantable medical device's operation to suit the needs of a particular patient. Such data includes the basic timing intervals used during operation of the pacemaker 10 and AV delay values and hysteresis AV delay values in particular.

Further, data sensed during the operation of the implantable medical device 10 may be stored in the memory MEM 64 for later retrieval and analysis.

A telemetry circuit TEL 66 is further included in the implantable medical device 10. This telemetry circuit TEL 66 is connected to the control unit CTRL 62 by way of a suitable command/data bus (not shown). Telemetry circuit TEL 66 allows for wireless data exchange between the implantable medical device 10 and some remote programming or analyzing device which can be part of a centralized service center serving multiple pacemakers.

The implantable medical device 10 in FIG. 3a is referred to as a three chamber pacemaker/cardioverter/defibrillator because it interfaces with the right atrium 26, the right ventricle 28 and the left ventricle of the heart 12. Those portions of the pacemaker 10 that interface with the right atrium, e.g., the lead 14, the P-wave sensing stage A-SENSE 56, the atrial stimulation pulse generator A-STIM 50 and corresponding portions of the control unit CTRL 62, are commonly referred to as the atrial channel. Similarly, those portions of the pacemaker 10 that interface with the right ventricle 28, e.g., the lead 16, the R-wave sensing stage RV-SENSE 58, the ventricular stimulation pulse generator RV-STIM 52, and corresponding portions of the control unit CTRL 62, are commonly referred to as the ventricular channel.

In order to be able to detect periods of physical activity of a patient indicating that the patient is awake and in order to allow rate adaptive pacing in a DDDR or a DDIR mode, the pace-maker 10 further includes a physiological sensor ACT 68 that is connected to the control unit CTRL 62 of the pacemaker 10. While this sensor ACT 68 is illustrated in FIG. 3 as being included within the pacemaker 10, it is to be understood that the sensor may also be external to the implantable medical device 10, yet still be implanted within or carried by the patient. A common type of sensor is an accelerometer, such as a piezoelectric crystal, mounted to the case of the pacemaker.

Other types of physiologic sensors are also known, such as sensors that sense the oxygen content of blood, respiration rate, blood pH, intra-cardiac impedance changes, and the like. The type of sensor used is not critical to the present invention. Any sensor capable of sensing some physiological parameter relatable to physical activity of a patient can be used. Such sensors are commonly used with "rate-responsive" pacemakers in order to adjust the rate of the pacemaker in a manner that tracks the physiological needs of the patient. The output of sensor 68 represents an activity level.

By means of the output signal of activity sensor 68, the control unit 62 is able to assign each intrinsic heart rate to an activity thus enabling collection of intrinsic heart rate value for a patient's state of rest and a patient's state of exercise separately.

The control unit CTRL 62 is adapted to determine an adequate heart rate or stimulation rate in any manner known as such.

For impedance measurement, an impedance determination unit 70 is provided. Impedance determination unit 70 comprises a constant current source 72 that is connected or can be connected to electrodes for intracorporeal placement as shown in FIG. 2. In order to allow for a plurality of impedance measurement electrode configurations, preferably some means of switching is provided between the constant current source 72 and the electrode terminals of the implantable medical device 10. The switch is not shown in FIG. 3. Rather, particular impedance measurement configurations are shown as examples.

Similarly, a voltage measuring unit 74 for measuring a voltage corresponding to a current fed through a body by said constant current source is provided and can be connected to a number of electrodes although a switch for switching between these configurations is not shown in FIG. 3.

As an alternative to constant current source 72 a constant voltage source can be provided to generate the forcing function. Then, the measuring unit will be adapted to measure a current strength of a current fed through a body by said constant voltage source.

Both, constant current source 72 and voltage measurement unit 74, are connected to an impedance value determination unit 76 that is adapted to determine an impedance value for each measuring current pulse delivered by the constant current source 72. The configuration shown in FIG. 3a is Quadrapolar #2 from Table 1 above. Connections from 72 and 74 to the pacemaker and ICD leads are dynamically reconfigurable to, among other things, any of the rows of Table 1.

Further, an evaluation unit 78 is provided either as a separate unit or as part of control unit CTRL 62 as depicted in FIG. 3. The evaluation unit 78 is connected to said impedance measurement unit 70 and is adapted to evaluate a sequence of consecutive impedance values determined by said impedance measurement unit. The evaluation unit 78 comprises a signal generator module (not shown) to construct the intracardiac impedance or conductance signal reflecting the time course of the impedance measurement unit's output signal and its derivative.

The evaluation unit 78 further comprises a filter module (not shown) to filter the intra-cardiac impedance signal.

The evaluation unit 78 is further connected to the right ventricular stimulation stage RV-STIM 52 and the right ventricular sensing stage RV-SENS 58 in order to receive signals representing cardiac events, namely right ventricular stimulation events RVp or right ventricular sense events RVs, respectively.

Figure 3B:
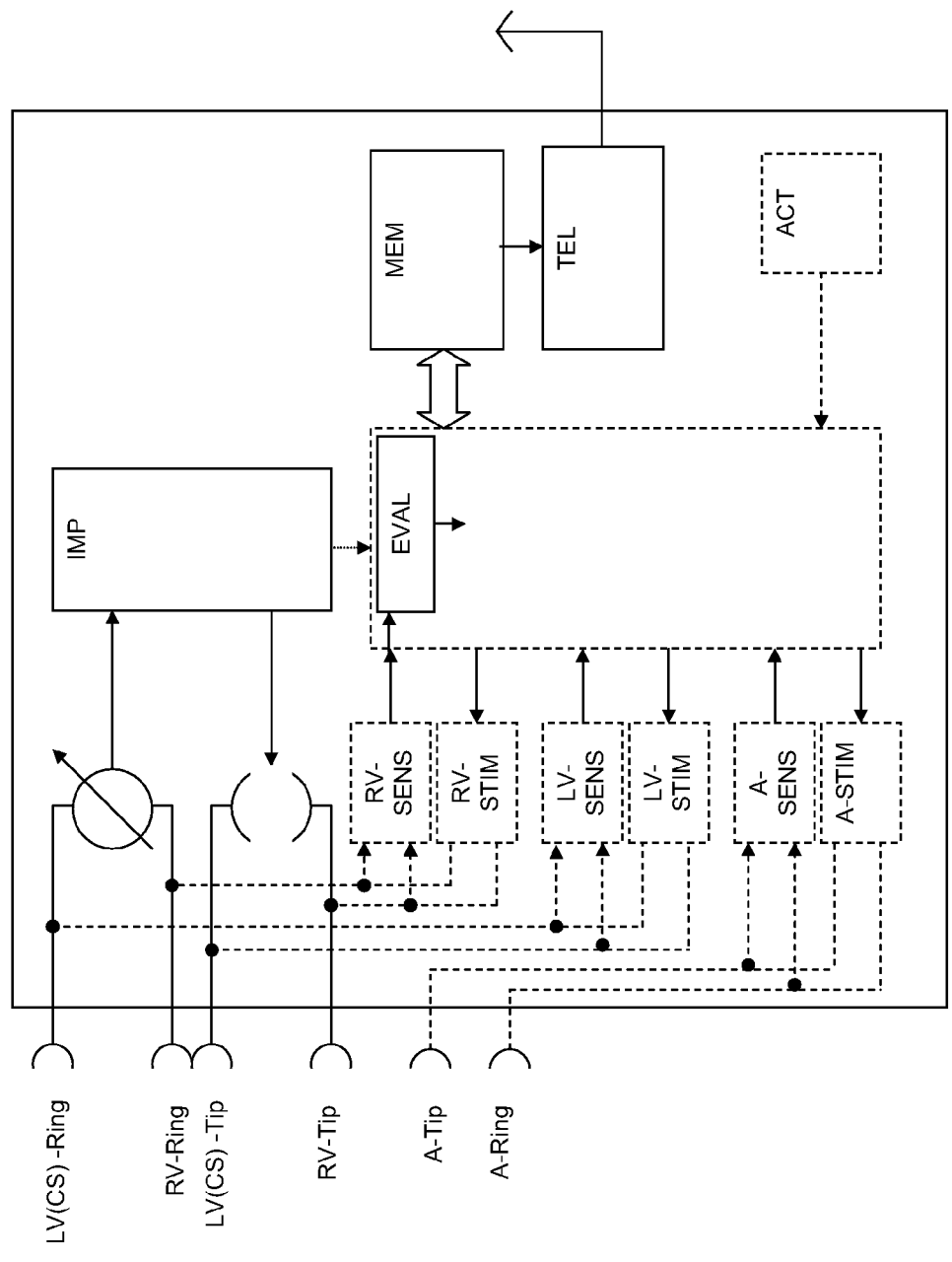
Figure 3C:
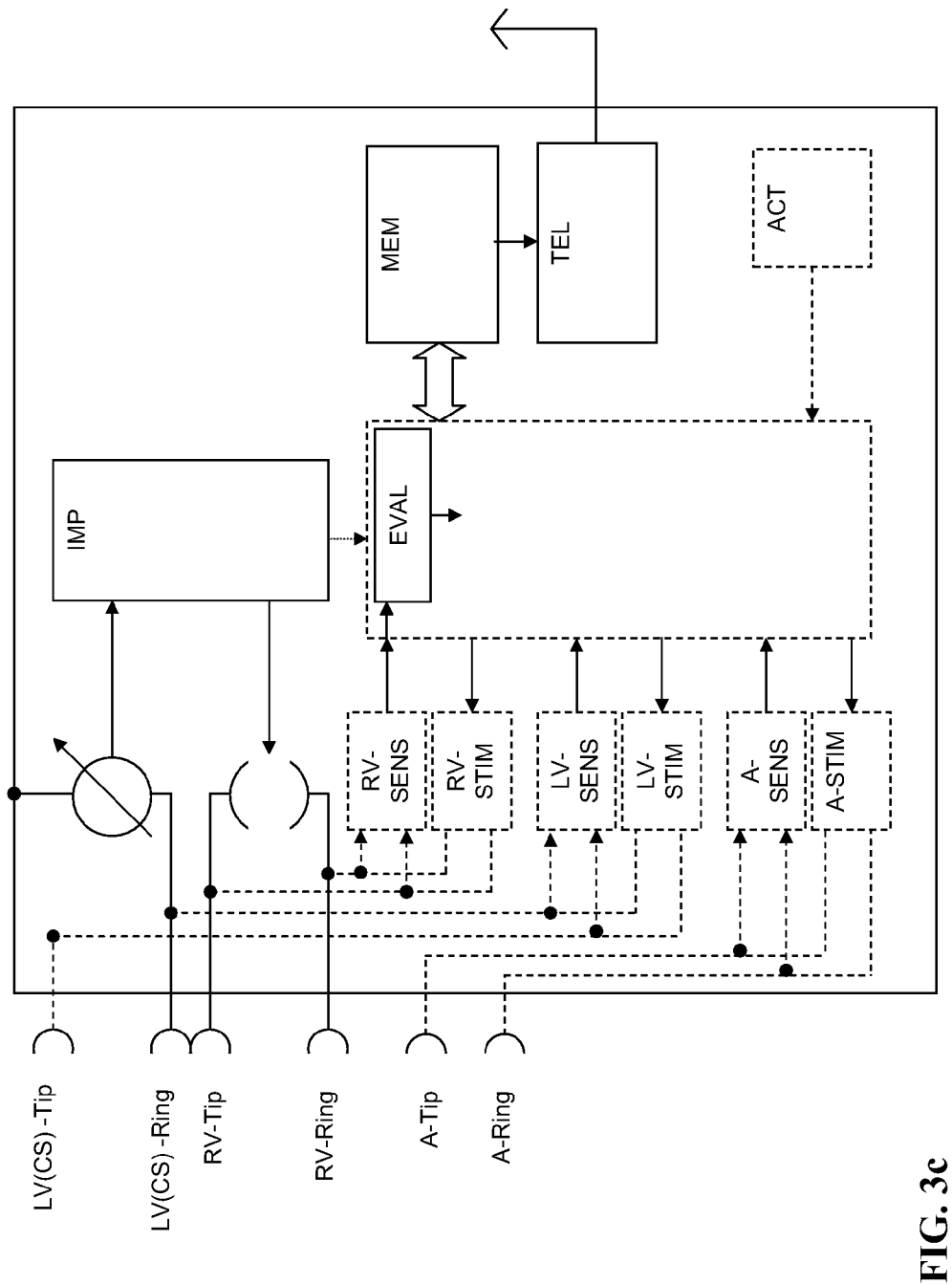

The constant current source 72 has its two poles connected to different connectors for different electrodes as for example the right ventricular tip electrode and the right ventricular ring electrode (FIGS. 3a and 3c) or the left ventricular tip electrode and the right ventricular tip electrode (FIG. 3b). The voltage measuring unit 74 has two poles connected to, for example, a connector for the left ventricular tip electrode and the left ventricular ring electrode (FIG. 3a) or the left ventricular ring electrode and the right ventricular ring electrode (FIG. 3b) or the left ventricular ring electrode and the pacemaker can 12 (FIG. 3c). Thus, a quadropolar impedance measurement configuration is established.

Impedance measurement is carried out by injecting a constant current and sampling the resulting voltage.

The measuring current is preferably pulsed. Typically, the measuring current will feature a pair of pulses wherein two non-overlapping constant current pulses of opposite polarity constitute a single biphasic pulse. A time gap is provided between consecutive biphasic pulses which is significantly longer than the duration of a single biphasic pulse. The constant current pulses within one biphasic pulse are each of the same intensity and duration. They only have different polarities. The typical value for the intensity of the constant current pulses is between 50 µA and 600 µA. The typical pulse duration of a single constant current pulse is about 15 µs.

The time gap between each consecutive biphasic pulse may be 500 times longer than the duration of a single constant current pulse. The two constant current pulses of opposite polarity within a biphasic pulse may, alternatively, also be separated by a time gap. This time gap, however, will be very short compared to the time gap between consecutive biphasic pulses. Furthermore, consecutive biphasic pulses may be phase alternating such that a first biphasic pulse, for example, will begin with a positive constant current pulse whereas the following biphasic pulse will begin with a negative constant current pulse and end with a positive constant current pulse.

The most preferred quadrupolar configuration for impedance measurement is the configuration as depicted in FIG. 3a wherein current injection will occur between right ventricular tip electrode and right ventricular ring electrode and voltage measurement will occur between the left ventricular tip and the left ventricular ring electrode.

Figures 4A, 4B:
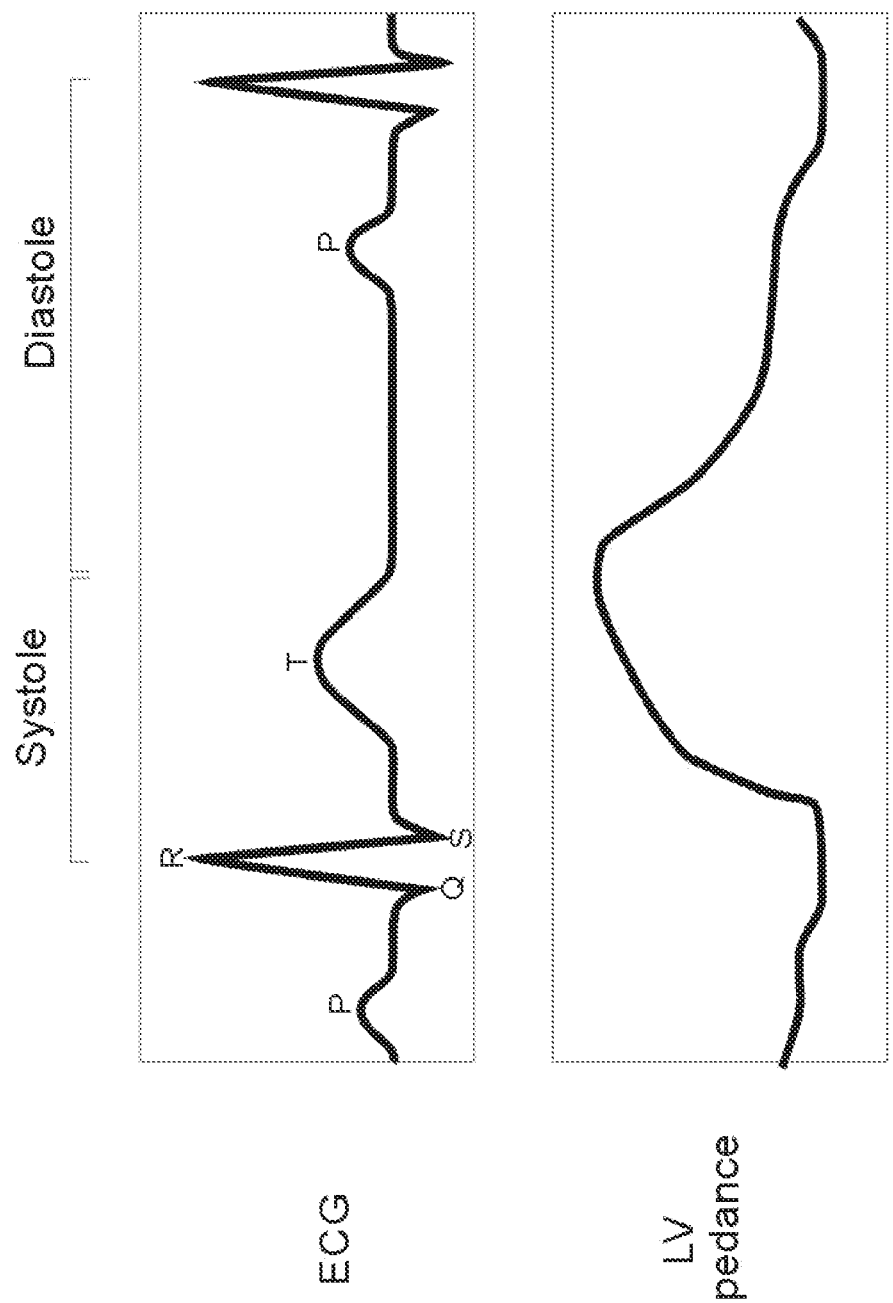
FIG. 4a shows an outline of an electrocardiogram over somewhat more than one cardiac cycle.
FIG. 4b shows a typical curve of the intracardial impedance in synoptic illustration to the curve of the electrocardiogram in FIG. 4A.
Figure 5:
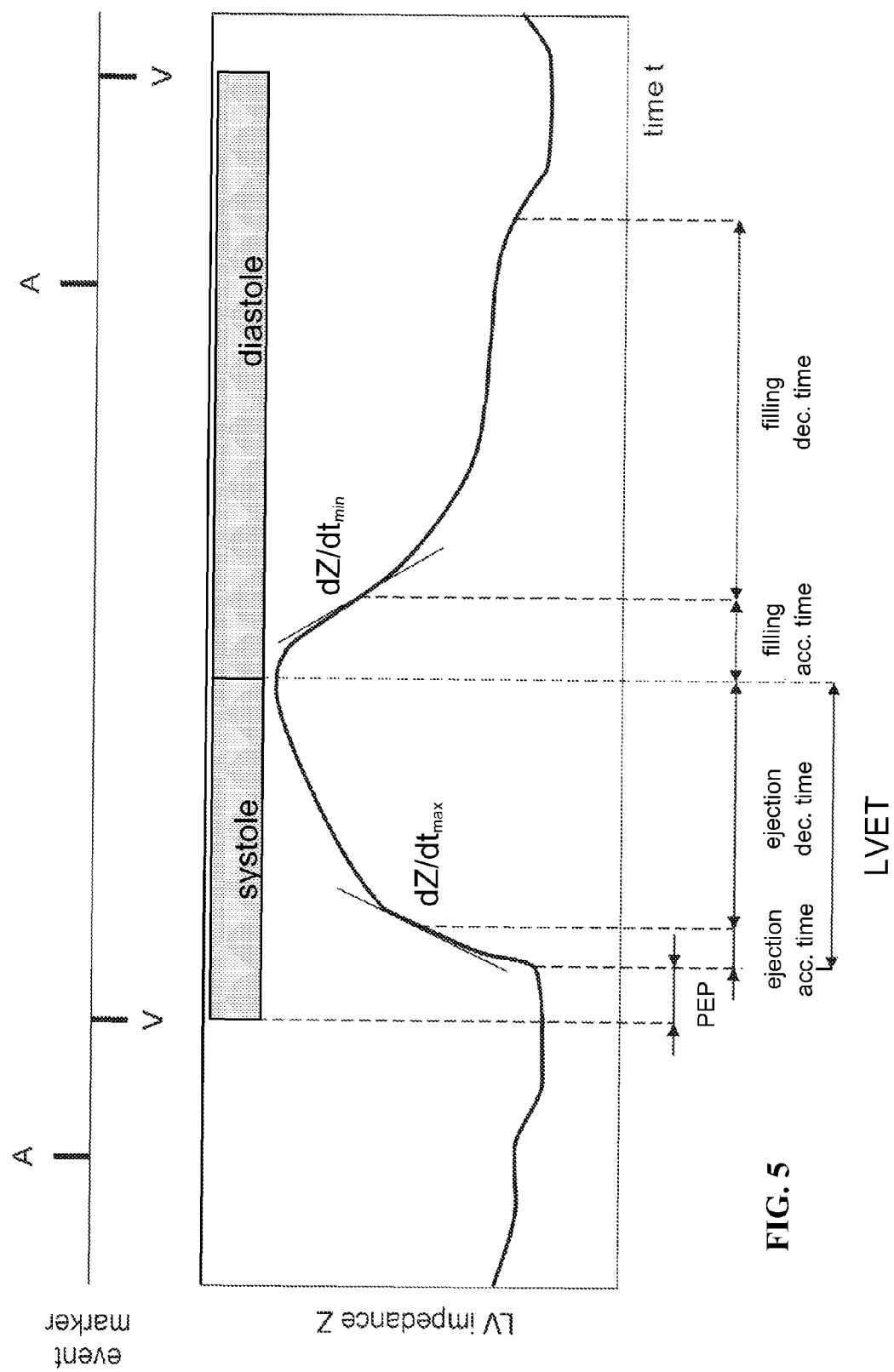
FIG. 5 shows a more differentiated illustration of the curve of the intracardiac impedance to explain essential parameters related to the impedance curve.

In FIG. 4b a typical time course of the left ventricular impedance is depicted. FIG. 4a shows a typical electrocardiogram. When the left ventricle has its smallest volume at the end of the systole (contraction of the ventricle) the impedance has a maximum. As shown in FIG. 5 the time course of the impedance inversely reflects the time course left ventricular volume.

The main purpose of the sensing stages 56, 58 and 60 is to detect a natural (intrinsic) stimulation of the respective heart chamber in order to generate a sense event signal like an atrial sense event As, a right ventricular sense event RVs and a left ventricular sense event LVs. These sense events are processed by the control unit CTRL 62 in order to inhibit a delivery of a stimulation pulse when the pacemaker is operating in a demand mode or in order to determine a time interval between an atrial event and a point of time, when the course of the left ventricular intracardiac impedance reaches its minimum value, see below.

Another type of event to be processed by the control unit CTRL 62 would be the delivery of a stimulation pulse to a respective heart chamber. Delivery of a stimulation pulse causes a paced event such as an atrial paced event Ap, a right ventricular paced event RVp and a left ventricular paced event LVp.

According to a preferred embodiment of the invention, different optimal time delays for different stimulation (pacing) rates and thus for different states of metabolic demand are determined. Therefore, memory MEM 64 is provided and connected to control unit CTRL 62 which is adapted to store optimal time delays such as optimal AV-delays AVD_opt and optimal VV-delays VVD_opt for different states of exertion.

Memory MEM 64 also serves for storing transient values for a measured maximum impedance (end systolic impedance ESZ) and tested time delays associated therewith as disclosed in more detail further below.

The evaluation unit EVAL 78 acts as a maximum impedance detector and is adapted to determine a maximum impedance value for each heart cycle which establishes a second fiducial point related to the time course of intracardiac impedance. For this purpose the evaluation unit EVAL 78 is connected to the impedance measuring stage IMP 76. Maximum impedance values ESZ are stored in association with said time delays in memory MEM 64 for further processing by the control unit CTRL 62.

Processing may further include deriving average minimum impedance values EDZ_avg and optimal time delays AVD_opt or VVD_opt, respectively.

According to the invention, evaluation unit EVAL 78 is adapted to determine a measured time delay between a cardiac event such, e.g. a ventricular event RVs or RVp that represents a first fiducial point related to the time course of an intracardiac electrogram and a minimum impedance value in the time course of the intracardiac impedance that is related to the cardiac event and that forms the second fiducial point in each heart cycle.

The evaluation unit 78 is further adapted to determine a plurality of such measured time delays and to determine the variance of this plurality of time delays. The variance represents myocardial dispersion.

The connection between an electrocardiogram (ECG) and the curve of the left-ventricular impedance will now be explained briefly on the basis of FIGS. 4A and 4B. FIG. 4A shows a typical electrocardiogram and FIG. 4B shows a typical curve of the left-ventricular impedance in synoptic assignment to the electrocardiogram.

As noted, the electrocardiogram results from electrical potentials of the myocardium, as they occur together with the contraction and the relaxation of the myocardium. A contraction of the cardiac muscle tissue—the contraction of the left ventricle here—is triggered by an electrical potential (an electrical excitation), which results in depolarization of the cardiac muscle cells and, originating from an excitation location, propagates to the entire myocardium of a ventricle and thus results in contraction of the ventricle. These electrical potentials resulting in depolarization of the cardiac muscle cells and thus contraction of the cardiac tissue may be recognized in the electrocardiogram as R waves. The repolarization of the cardiac tissue, which accompanies the relaxation of the myocardium, is coincident with the T waves recognizable in the electrocardiogram. A P wave results from the electrical potentials that accompany the contraction of the atrium.

As may be seen from the curve of the left-ventricular impedance in FIG. 4B, the impedance has a minimum approximately at the instant of the occurrence of the R wave. At this instant, the ventricle has its greatest volume and therefore has the lowest impedance. The ventricle begins to contract with a slight delay after the occurrence of the R wave, so that the impedance increases until it reaches its maximum when the ventricle is maximally contracted. The phase of the rise of the left-ventricular impedance accompanies the ejection phase (systole) of the heart, in which blood is pressed out of the ventricle through the aortic valve into the aorta. After the ventricle has reached its maximally contracted state, the cardiac muscle tissue (myocardium) repolarizes. The beginning of the repolarization may be recognized in the electrocardiogram as a T wave and results in the left-ventricular impedance falling again after reaching the impedance maximum. The drop of the left-ventricular impedance reflects the volume of the left ventricle, which enlarges with increasing relaxation of the myocardium. A contraction of the atrium, which precedes a P wave in the electrocardiogram, results in further filling of the ventricle and a corresponding volume enlargement and thus a further impedance drop until finally a renewed contraction of the ventricle occurs.

According to preferred embodiments of the invention one or more of the instants and values which the control unit CTRL 62 may ascertain to determine the cardiac function parameter values are shown in FIG. 5. Most of the cardiac function parameters whose values the control unit may be implemented to determine are also plotted in FIG. 5.

In addition, it is indicated in FIG. 5 that the evaluation unit EVAL assigns values and instants to be inferred from the impedance curve to the instants of the occurrence of an R wave and a P wave in the electrocardiogram by analyzing corresponding marker signals RV, LV and A. These marker signals are generated whenever the right ventricular sensing stage RV-SENS, the left ventricular sensing stage LV-SENS, or the right atrial sensing stage A-SENS detects a respective cardiac event, that is, whenever the right ventricular electrogram, the left ventricular electrogram, or the right atrial electrogram exceeds a predetermined threshold value.

It may be inferred from FIG. 5 that the systole, i.e., the ejection phase, extends from the instant of the depolarization of the ventricular myocardium, characterized by a RV sense event—until reaching the minimum ventricular chamber volume—characterized by the maximum of the impedance curve. The diastole extends in time from the instant of the occurrence of the impedance maximum up to the next ventricular depolarization.

The pre-ejection phase PEP extends from the beginning of the ventricular depolarization (V marker) up to the clear beginning of an impedance increase. The ejection acceleration phase extends from this clear rise of the left-ventricular impedance up to reaching the instant in which the impedance curve has its greatest positive slope, i.e., the gradient of the impedance curve is greatest. The ejection delay time extends from the instant of the occurrence of the maximum slope (maximum gradient) of the impedance curve until reaching the impedance maximum. Ejection acceleration time and ejection delay time, taken together, result in the left-ventricular ejection time (LVET). Upon reaching the maximum left-ventricular impedance, the ejection phase of the heart, i.e., the systole, ends and the filling phase, i.e., the diastole, begins.

The diastole begins with the filling acceleration time, which extends in time from the occurrence of the maximum of the impedance curve up to the instant of the occurrence of the maximum negative slope of the impedance curve (maximum negative gradient dZ/dtMin). The filling delay time begins with the instant of the occurrence of the maximum negative gradient and extends up to the occurrence of the apex of a parabolic approximation function of the impedance curve, beginning with the instant of the occurrence of the maximum negative slope.

Control unit CTRL 62 may be adapted to derive different risk marker signals from the alternations and variabilities thus ascertained. Such risk marker signals may, for example, be used as short-term predictors for life-threatening cardiac arrhythmias, since alternations or variabilities of cardiac function parameter values derived from the impedance may be precursors of a ventricular fibrillation. The prediction of a ventricular fibrillation goes back to the analysis of a few more recent cardiac cycles, i.e., it represents a short-term analysis. A long-term analysis of the risk parameters may be used for predicting the risk of sudden cardiac death or for observing the course of a cardiac illness such as severe congestive heart failure.

Furthermore, control unit CTRL 62 may be implemented to optimize electrotherapy by the cardiac pacemaker 10, i.e., in particular to set the parameters decisive for the electrical stimulation of the heart, such as the instant and strength of stimulation pulses, as a function of the cardiac function parameter values ascertained by control unit CTRL 62. The treatment parameters optimized in this way include the stimulation rate and the atrioventricular delay interval. In two-chamber pacemakers (biventricular pacemakers), the control unit CTRL 62 may also be implemented to optimize the intraventricular delay time or the biventricular stimulation mode on the basis of the cardiac function parameter values derived from the impedance. In regard to the biventricular stimulation mode, the control unit CTRL 62 may determine whether the stimulation is to be performed only in the left ventricle, only in the right ventricle, or whether a stimulation of both ventricles is to be performed as a function of which stimulation form results in the greatest value of the maximum of the gradient of the impedance curve during the systole. The control unit CTRL 62 may further optimize the interventricular delay time (VVI) in the same way.

By means of the device illustrated above and according to the invention, detection and monitoring of myocardial performance, to provide an indication of changes in the status of heart failure (HF) patients, is accomplished by monitoring the dispersion characteristics of the intracardiac electrogram (IEGM), versus the intracardiac impedance measurements to detect changes in the electromechanical coupling of these events within the heart.

In one preferred embodiment, the information could be used to identify the development of electromechanical delays and/or the development of intra- or inter-ventricular dyssynchrony that precede clinical signs and symptoms of heart failure (HF).

In another preferred embodiment, the information could be used to modify (manually or automatically) device parameters to optimize cardiac resynchronization therapy (CRT). In addition, it could provide objective data to optimize medical therapy for the treatment of HF.

Whatever the embodiment, any inter-cardiac or intra-cardiac impedance configuration (bipolar, tripolar, quadrupolar) may be used, including, but not limited to, pathways involving the RV only, LV only, between the RV and LV, or any combination of pathways. In addition, sensing of electrical events may involve a plurality of sensing electrodes placed within the chambers, blood vessels, or on the surface of the heart.

Figure 6:
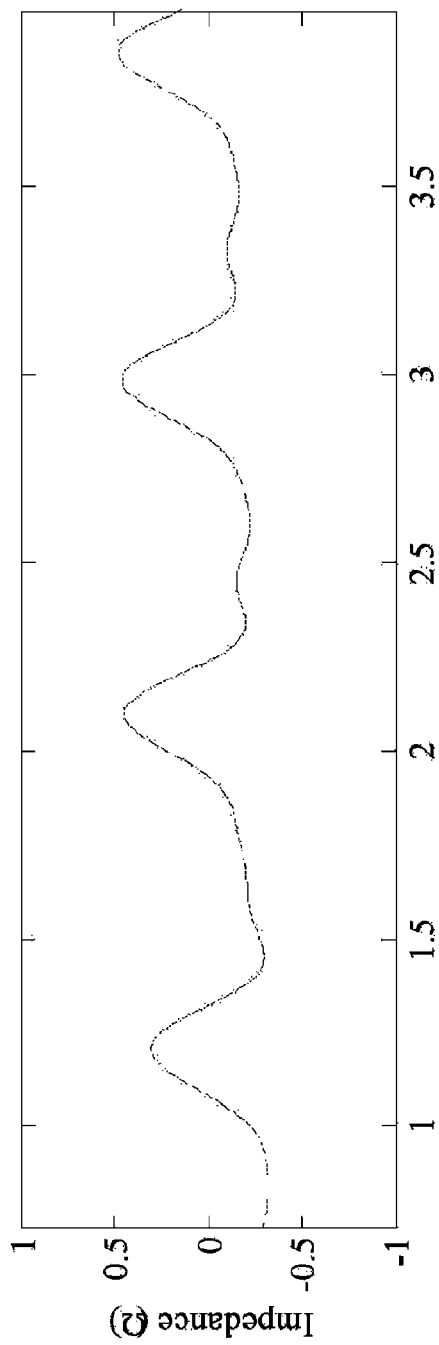
FIG. 6 shows a curve of the intracardiac impedance over multiple cycles to illustrate an alternation.
Figure 7:
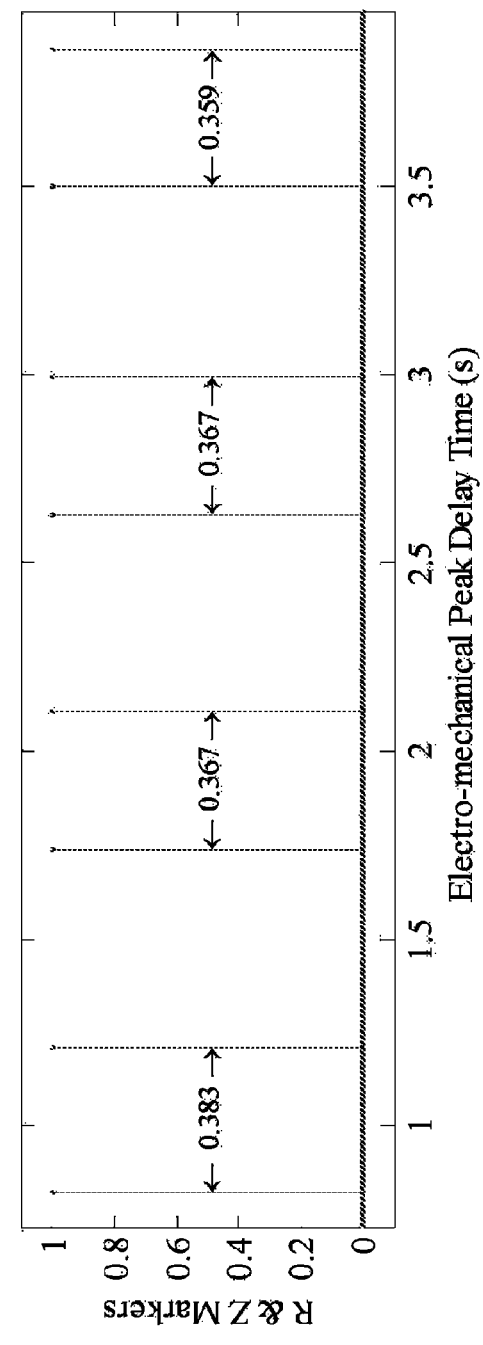
FIG. 7. shows the timing relationship between the electrical and the mechanical events of the cardiac cycle.

FIG. 6 shows the relationship between events in the intracardiac electrogram (IEGM) and their corresponding events in the impedance waveform. The upper half of FIG. 6 shows the representation of the hemodynamic systolic events in the cardiac component of the impedance waveform as cyclic peaks. The lower half (FIG. 7) shows markers for the IEGM RV sensed event (pointed at by left arrows) and the impedance systolic peak (pointed at by right arrows). The conventional IEGM-based heart rate is derived from the cycle times between successive markers pointed at by left arrows. The cycle time of the impedance systolic peak is determined by analyzing successive markers pointed at by right hand arrows. The electro mechanical coupling is determined by the time difference between left-right arrow pairs.

Figure 8:
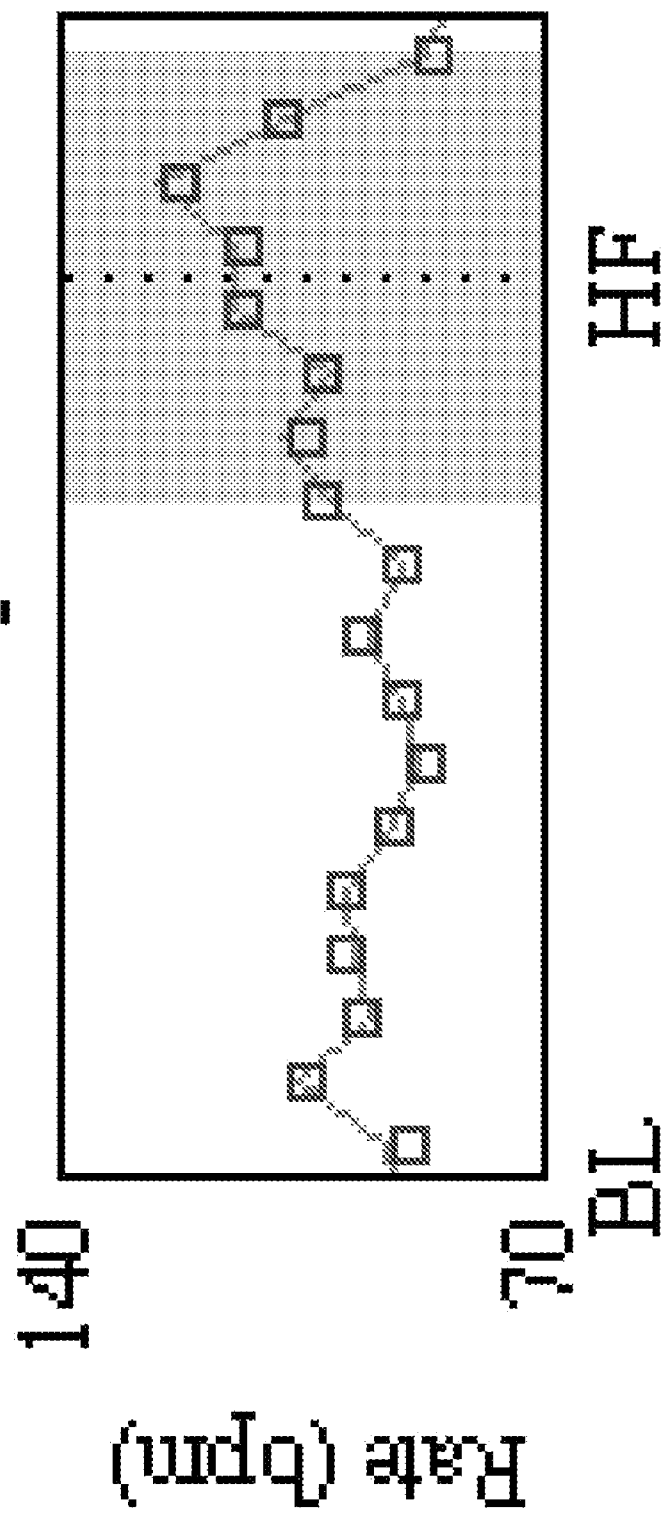
FIG. 8 shows a comparison of the IEGM and impedance based heart rates.

The statistics, such as, averages and variability of cycle times based on the IEGM (heart rate), cycle times based on the impedance systolic peak events, and statistics of the interaction between these two are measures of interest here. FIG. 8 shows that the conventional IEGM-based heart rate and the heart rate derived from the cycle time of the impedance systolic peak coincide throughout various hemodynamic states. In the figure, the subject starts out with a heart rate between 70 and 100 bpm. The unbroken line shows daily averages in heart rate using IEGM R wave cycle time. The squares are daily averages of heart rate determined by cycle time of impedance systolic peak. The gray patch in the figure shows a period of transition into HF. At the point of the vertical dotted line(¦), intervention to alleviate HF occurs. Because of the 1:1 relationship between depolarizations and resulting systolic events, a high degree of coupling of the rates determined by these two signals is expected.

Figure 9:
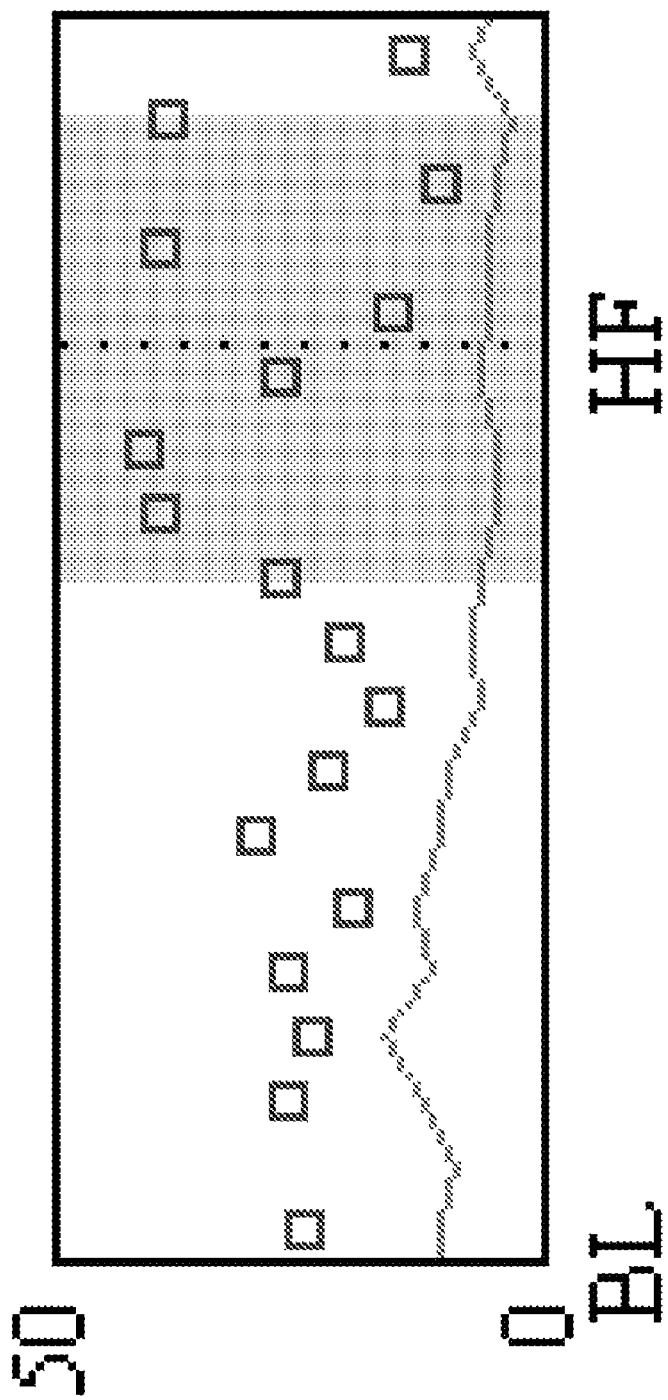
FIG. 9 shows a comparison of the IEGM and impedance based heart rate dispersions.

FIG. 9 shows a comparison of IEGM versus impedance systolic peak (end systolic impedance ESZ) based on the analysis of the dispersions of the two signals. The figure is organized similarly to the previous, though the value of points in this figure is the inter quartile range (IQR) of the values used to generate the average. Although the averages of the two signals for determining heart rate coincide, the dispersion of these two signals around a central daily value is not the same. It can be seen that as the subject enters HF, dispersion of the IEGM-based cycle time decreases as expected due ostensibly to increased sympathetic tone. The dispersion of the impedance systolic-based cycle time increases as the subject passes through HF. After HF intervention, the dispersions of the two signals begin to coincide again. This divergence in behavior between the two signals suggests that the relationship between them changes during HF.

Figure 10:
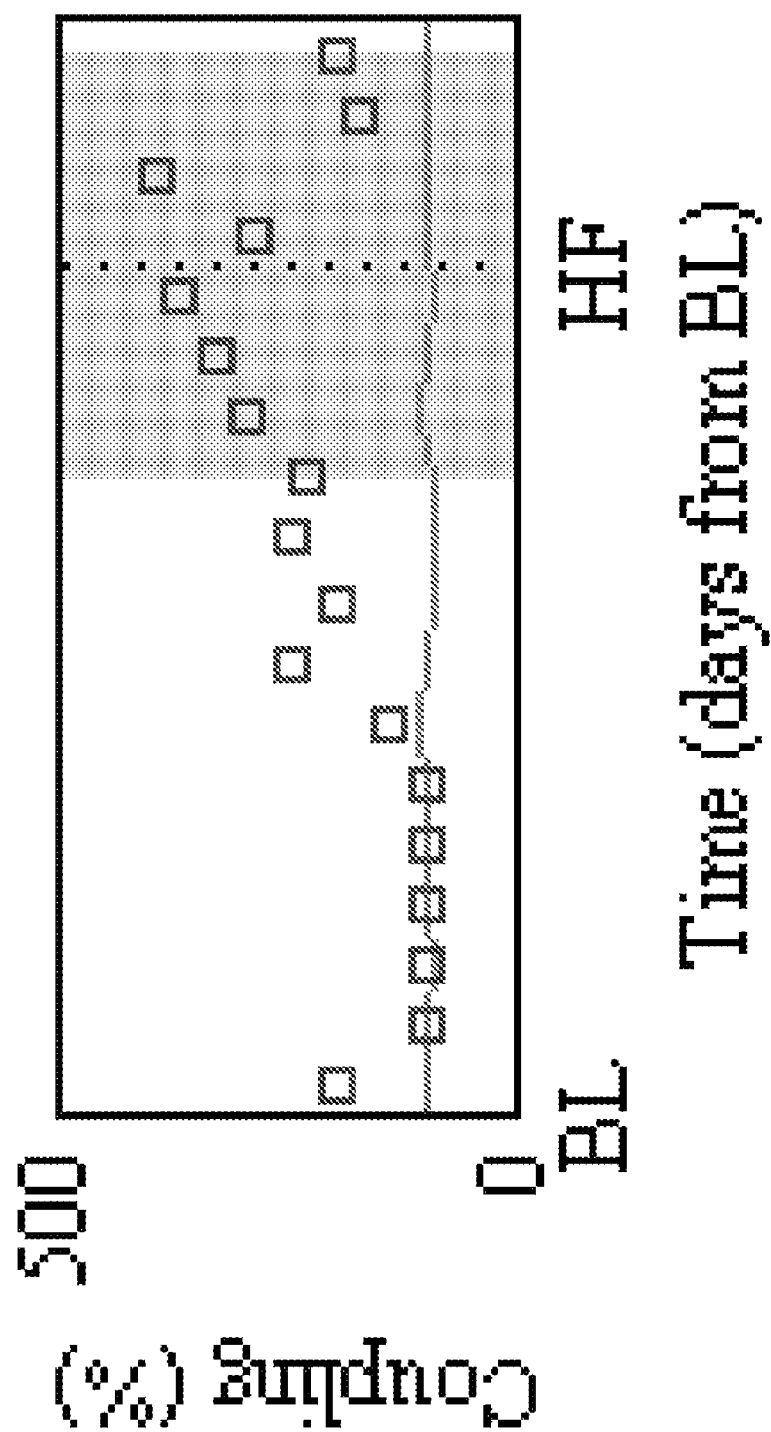
FIG. 10 shows the de-Coupling between IEGM R wave and impedance systolic peak events.

FIG. 10 shows that electrical (conduction system) control of heart rate and the mechanical response are becoming uncoupled by analysis of the time elapsed between the R Wave detection and the impedance systolic peak (end systolic impedance ESZ). The unbroken line is the daily average of coupling time (average of time between pairs of left right arrows in FIG. 6). The value deviates very little around 100% of the baseline (BL) value even through the HF physiologic state. The square symbols are the dispersion (IQR) of the values used to calculate the daily averages. Initially, the dispersion of the coupling time remains nominal, essentially 'coupled' to the IEGM. In the HF state, it can be seen that the dispersion of the electromechanical coupling time increases several times ($\geqq 400\%$ in this example). The mechanical response 'de-couples' due to another driving function, in this case, the RV and LV Dyskinesis (dyssynchrony) that ensued with HF in this subject. Again as HF intervention occurs, the dispersion of coupling trends downward toward baseline.

In summary, it is the divergence of the statistical properties of IEGM and impedance based cycle times that indicates a state of HF, while their convergence shows response to HF intervention.

If it is desired to separate two or more mixed signals, for example, the coupling between impedance systolic peaks of RV and LV, at least one of the following is necessary:

Either a single measurement channel of impedance capable of resolving components of interest, or two or more time synchronized measurement channels each individually configurable to resolve components of interest.

According to a preferred embodiment, the control unit CTRL 62 is adapted to cause a transmission of data acquired via the evaluation unit 78 routinely (daily) and as necessary (in case of an alert) via the telemetry circuit TEL 66 to a remote station to be used as part of a Heart failure assessment package of information available via a remote service center.

Returning to a best mode presently contemplated for realizing the core of the invention, that is, establishing an analysis of mechanical and electrical coupling in the heart. The evaluation unit 78 is adapted to:

a) Measure the beat to beat interval of the electrogram at sufficient time resolution to reveal the heart rate variance.

b) Identify in (a) a fiducial point, such as, threshold crossing of the electrogram.

c) Calculate statistics of the threshold crossings in the measurement, such as, inter-quartile range or SD50.

d) Concurrently, sample the intracardiac impedance separating the cardiac ($Z_{cardiac}$) and respiratory ($Z_{resp}$) source signals from each other.

e) Identify in $Z_{cardiac}$ a fiducial point, such as, each peak of the systolic artifact resulting from each threshold crossing of the electrogram.

f) Calculate the measured time delay between each threshold crossing of the electrogram to each $Z_{cardiac}$ peak.

Preferably, the evaluation unit 78 is further adapted to:

g) calculate statistics of the threshold crossings to $Z_{cardiac}$ peak delay (linkage) using a dispersion measure, such as, interquartile range or SD50.

h) calculate the $Z_{cardiac}$ peak beat to beat interval such that it is the sum of the beat to beat interval (a) and the $Z_{cardiac}$ peak delay (f) for each beat and constitutes a mechanical analog to (a).

Further, statistics of (h) may be calculated as well. These statistics may be reduced to a single value for ease of evaluation, such as, an index of dispersion based on the distance between upper and lower confidence limits.

A change from a baseline state of LV function to a worsening state, will be characterized by an increased measure of dispersion in (g) and (h), even if dispersion is stable or shrinks in (c). This is caused by an unlinking of the electrical and mechanical aspects of a heart beat. In the IEGM, heart rate variability (HRV) indicates health and diminishing HRV indicates increased cardiac stress. In the mechanical aspect of the heart beat, a certain amount of HRV indicates health, such as, due to respiratory modulation. However, increased Cycle Time Variability in the mechanical signal indicates disruption of a coordinated mechanical event (dyskinesis or dyssynchrony). The inventors found that the conduction system behaved normally: no significant change in the interventricular conduction delay (IVCD), no indication of increased QRS width, and normal seeming diminishment of HRV as the spontaneous rate increased. Contrariwise, the $Z_{cardiac}$ peak Cycle Time Variability increased as IEGM HRV decreased and became most dispersed during HF where IEGM HRV was minimal. Dyssynchrony was confirmed by wall motion analysis. Likewise during resolution of HF, the $Z_{cardiac}$ peak Cycle Time Variability resumed approximation toward baseline dispersion levels.

Further alternatively, the interventricular conduction delay (IVCD) also has an electrical and mechanical counterpart whose linkage can be monitored to indicate relative states of health and compromised LV function. Consider that the apparatus in one embodiment is capable of simultaneous measurements of IEGM and impedance in multiple chambers, for example RV and LV. It should also be considered that the IEGM derived interventricular conduction delay take the place of (a) above and the corresponding delay between peak of the $Z_{cardiac}$ systolic artifacts in each chamber (RV and LV) take the place of (f), (g), and (h) above. Here again the statistics for the IVCD may be reduced to a single value, such as, the proportion of right before left versus left before right bundle branch indicating a preference and pattern of BB activation subject to evaluation by the sign test.

Other than depicted in FIG. 3, the evaluation unit may be part of the external device 80 or central service centre 90 to thus distribute computation by capability of the implantable medical device, the external device and the central service centre. In this case, the heart monitoring apparatus is distributed over one or more components of a distributed system.

The data acquired by the evaluation unit may be trended and a trigger may be provided if the trended data cross a prescribed threshold. This feature might be particularly useful in an automatic clinician notification system.

The invention provides for a number of advantages:

No additional leads or sensors are required beyond those that are already incorporated in state of the art CRM devices.

Impedance measurements can be made with customary pacing/defibrillation leads, including leads placed endocardially, epicardially, or thru the coronary sinus.

The information acquired can become part of the Home monitoring system, which provides early warning for detecting decompensating LV function, or developing heart failure.

The apparatus is capable to identify underlying physiologic (mechanical) changes that are latent in typical measures (electrogram) associated with LV failure or its resolution. Yet these parameter changes are understandable by clinicians, can be corroborated, and there are known therapies that can be implemented to correct the underlying problem(s).

A long term monitoring of the divergence of the R-wave versus the impedance systolic peak variability may provide a new approach to HF management and CRT optimization.

Although an exemplary embodiment of the present invention has been shown and described, it should be apparent to those of ordinary skill that a number of changes and modifications to the invention may be made without departing from the spirit and scope of the invention. This invention can readily be adapted to a number of different kinds of heart monitoring systems or apparatus or implantable medical devices by following the present teachings. All such changes, modifications and alterations should therefore be recognized as falling within the scope of the present invention.

What is claimed is:

1. An implantable heart monitoring apparatus, comprising:
   at least one intracardiac electrode configured to pick up electric potentials of a myocardium of a heart's ventricle or atrium;
   at least one sensing stage connected to said at least one intracardiac electrode, wherein said at least one sensing stage is configured to process electric signals that represent a time course of said electric potentials;
   at least one mechanical action detection stage configured to generate a geometry signal that reflects mechanical action of a heart chamber, said geometry signal having a time course that reflects a change of a heart chamber's geometry wherein said at least one mechanical action detection stage comprises an impedance measuring stage within said implantable heart monitoring apparatus that is connected to said at least one intracardiac electrode and configured to determine a time course of an intracardiac impedance or conductance signal that reflects an intracardiac impedance or conductance detected with said at least one intracardiac electrode, wherein said intracardiac impedance or conductance signal is utilized as said geometry signal;
   an evaluation unit coupled with said at least one sensing stage and to said at least one mechanical action detection stage, said evaluation unit configured to determine
      a first fiducial point in the time course of said electric potentials and
      a second fiducial point in the time course of said geometry signal,
      wherein said first fiducial point and said second fiducial point belong to a same heart cycle, and wherein said evaluation unit is further configured to determine
         a measured time delay between said first and said second fiducial points that represent a difference in time between corresponding points in said time course of said electric potentials versus said time course of said geometry signal respectively;
   said evaluation unit further configured to repeat said determination of said measured time delay between two fiducial points to thus determine a plurality of measured time delays
   and to determine
      a variance of said plurality of measured time delays based on said time course of said electric potentials versus said time course of said geometry signal,
   or
      a divergence of statistical properties of cycle times that are based on said time course of said electric potentials versus cycle times that are based on said time course that reflect said change of said heart chamber's geometry; and,
   generate an output signal that indicates a state of heart failure based on said time course of said electric potentials versus said time course of said geometry signal.

2. The implantable heart monitoring apparatus according to claim 1, wherein the evaluation unit is configured to determine a peak in said time course of the intracardiac impedance or a minimum in the time course of the intracardiac conductance as a second fiducial point related to said impedance or conductance, respectively.

3. The implantable heart monitoring apparatus according to claim 1, wherein said at least one sensing stage is configured to detect cardiac events that represent a depolarization of the myocardium wherein said at least one sensing stages is configured to process said electric signals that represent said time course of said electric potentials, wherein said a cardiac event selected from said cardiac events marks a first fiducial point in said time course of said electric potentials.

4. The implantable heart monitoring apparatus according to claim 1, wherein the evaluation unit is configured to determine the divergence of the statistical properties of IEGM and impedance based cycle times and generate an output signal that indicates said state of said heart failure, when the divergence exceeds a predetermined threshold value.

5. The implantable heart monitoring apparatus according to claim 1, wherein the evaluation unit is configured to separate cardiac ($Z_{cardiac}$) and respiratory ($Z_{resp}$) source signals in the intracardiac impedance signal from each other.

6. The implantable heart monitoring apparatus according to claim 1, wherein the evaluation unit is configured to:
   measure a beat to beat interval measurement of the time course of said electric potentials at sufficient time resolution to reveal a heart rate variance;
   identify a fiducial point, comprising threshold crossing of the time course of said electric potentials;
   calculate statistics of the threshold crossings in the measurement;
   concurrently, sample the intra cardiac impedance separating cardiac ($Z_{cardiac}$) and respiratory ($Z_{resp}$) source signals from each other;
   identify in $Z_{cardiac}$ a fiducial point, comprising each peak of a systolic artifact resulting from each threshold crossing of the time course of said electric potentials; and,
   calculate a measured time delay between each threshold crossing of an electrogram to each $Z_{cardiac}$ peak.

7. The implantable heart monitoring apparatus according to claim 6, wherein the evaluation unit is further configured to:
   calculate statistics of threshold crossings to $Z_{cardiac}$ peak delay (linkage) using a dispersion measure wherein said dispersion measure comprises interquartile range or SD50; and,
   calculate a $Z_{cardiac}$ peak beat to beat interval such that it is the sum of the beat to beat interval and the $Z_{cardiac}$ peak delay for each beat and constitutes a mechanical analog to said measurement.

8. The implantable heart monitoring apparatus according to claim 1, wherein said time course of said electric potentials is a right ventricular intracardiac electrocardiogram and wherein said time course that reflects a change of a heart chamber's geometry is a right ventricular intracardiac impedance.

9. The heart monitoring apparatus according to claim 1, wherein said time course of said electric potentials is a right ventricular intracardiac electrocardiogram and wherein said time course that reflects a change of a heart chamber's geometry is a left ventricular intracardiac impedance.

10. A method for monitoring a heart's health state comprising:
   acquiring a signal that represents a time course of electric potentials with at least one intracardiac electrode configured to pick up electric potentials of a myocardium of a heart's ventricle or atrium;
   acquiring a geometry signal having a time course that reflects a change of a heart chamber's geometry using said at least one intracardiac electrode coupled with a impedance measuring stage within an implantable heart apparatus;
   determining a first fiducial point in the time course of said electric potentials;
   determining a second fiducial point in the time course of said geometry signal, said first fiducial point and said second fiducial point belonging to the same heart cycle;

determining a measured time delay between said first and said second fiducial point that represent a difference in time between corresponding points in said time course of said electric potentials versus said time course of said geometry signal respectively;

repeating said determining said measured time delay between two fiducial points to thus determine a plurality of measured time delays; and determining
- a variance of said plurality of measured time delays based on said time course of said electric potentials versus said time course of said geometry signal, or
- a divergence of statistical properties of cycle times that are based on said time course of said electric potentials versus cycle times that are based on said time course that reflect said change of said heart chamber's geometry; and generating an output signal that indicates a state of heart failure based on said time course of said electric potentials versus said time course of said geometry signal.

11. The method for monitoring a heart's health state according to claim 10 further comprising:

measuring a beat to beat interval of the time course of said electric potentials at sufficient time resolution to reveal a heart rate variance;

identifying a fiducial point, comprising a threshold crossing of the time course of said electric potentials;

calculating statistics of threshold crossings in the measurement;

concurrently, sampling intracardiac impedance values that represent said time course of said geometry signal and separating cardiac ($Z_{cardiac}$) and respiratory ($Z_{resp}$) source signals from each other;

identifying in $Z_{cardiac}$ a fiducial point, that includes each peak of a systolic artifact resulting from each threshold crossing of the time course of said electric potentials; and, calculating the measured time delay between each threshold crossing of an electrogram to each $Z_{cardiac}$ peak.

12. The method for monitoring a heart's health state according to claim 10 further comprising:

separating cardiac ($Z_{cardiac}$) and respiratory ($Z_{resp}$) source signals in the intracardiac impedance signal from each other.

13. The method for monitoring a heart's health state according to claim 10 further comprising:

calculating statistics of threshold crossings to $Z_{cardiac}$ peak delay (linkage) using a dispersion measure wherein said dispersion measure comprises interquartile range or SD50; and, calculating a $Z_{cardiac}$ peak beat to beat interval such that it is the sum of the beat to beat interval and the $Z_{cardiac}$ peak delay for each beat and constitutes a mechanical analog to said measurement.

* * * * *